United States Patent
Holden et al.

(10) Patent No.: US 10,851,041 B2
(45) Date of Patent: Dec. 1, 2020

(54) FOULING-RESISTANT DISTILLATION COLUMN AND PROCESS FOR THE MANUFACTURE OF COMPOUNDS

(71) Applicant: Dow Global Technologies LLC, Midland, MI (US)

(72) Inventors: Bruce S. Holden, Midland, MI (US); John W. Wilchek, Jr., Destrehan, LA (US)

(73) Assignee: Dow Global Technologies LLC, Midland, MI (US)

(*) Notice: Subject to any disclaimer, the term of this patent is extended or adjusted under 35 U.S.C. 154(b) by 289 days.

(21) Appl. No.: 14/901,444

(22) PCT Filed: Jun. 26, 2014

(86) PCT No.: PCT/US2014/044345
§ 371 (c)(1),
(2) Date: Dec. 28, 2015

(87) PCT Pub. No.: WO2014/210312
PCT Pub. Date: Dec. 31, 2014

(65) Prior Publication Data
US 2016/0368852 A1    Dec. 22, 2016

Related U.S. Application Data

(60) Provisional application No. 61/840,840, filed on Jun. 28, 2013.

(51) Int. Cl.
*B01D 3/00*     (2006.01)
*B01D 3/22*     (2006.01)
(Continued)

(52) U.S. Cl.
CPC .............. *C07C 67/54* (2013.01); *B01D 3/009* (2013.01); *B01D 3/22* (2013.01); *B01D 3/24* (2013.01)

(58) Field of Classification Search
CPC .......... C07C 67/54; B01D 3/009; B01D 3/22; B01D 3/24; B01D 3/14; B01D 3/16;
(Continued)

(56) References Cited

U.S. PATENT DOCUMENTS 2,161,247 A * 6/1939 Dearborn ............... C10G 11/00
                                                       208/113
2,534,870 A    12/1950 Kraft
(Continued)

FOREIGN PATENT DOCUMENTS

CN       1170610 A       1/1998
CN       101053700       10/2007
(Continued)

OTHER PUBLICATIONS

Bhanvase, B A, et al. "Internal Reboiler in Distillation Column." ResearchGate, Jun. 2007. <https://www.researchgate.net/publication/293736484>.*
(Continued)

*Primary Examiner* — Patrick Orme
(74) *Attorney, Agent, or Firm* — Brian L. Mutschler (57) ABSTRACT

Disclosed herein is a fouling-resistant system for the manufacture of a compound by distillation, the system including a reactant heating zone; a distillation column in fluid communication with the reactant heating zone wherein the distillation column comprises a plurality of distillation trays for removing by-products from the reactants, and wherein at least 20% of the plurality of distillation trays are baffle trays arranged in a staggered configuration; where each tray contacts an opposing portion of an inner wall of the distillation column from a portion contacted by a tray located above the tray and below the tray; and wherein the baffle trays are disposed in a lower portion of the distillation column.

10 Claims, 6 Drawing Sheets

(51) Int. Cl.
  *C07C 67/54* (2006.01)
  *B01D 3/24* (2006.01)
(58) Field of Classification Search
  CPC .......... B01D 3/26; B01D 3/324; B01J 19/006; B01J 2219/00247
  USPC ....................................................... 202/158
  See application file for complete search history.

(56) References Cited

U.S. PATENT DOCUMENTS

| | | | |
|---|---|---|---|
| 2,934,326 A | | 4/1960 | Strand |
| 3,083,148 A | | 3/1963 | Mojonnier |
| 4,543,219 A | * | 9/1985 | Yamato .................... B01D 3/18 261/109 |
| 6,436,245 B1 | * | 8/2002 | Nishimura ............... B01D 3/22 202/158 |
| 7,348,455 B2 | * | 3/2008 | Yada ........................ B01D 3/14 562/545 |
| 7,569,721 B2 | | 8/2009 | Patterson et al. |
| 2004/0222077 A1 | * | 11/2004 | Yada ........................ B01D 3/10 203/1 |
| 2009/0266107 A1 | | 10/2009 | Sing et al. |
| 2011/0005914 A1 | | 1/2011 | Trippeer et al. |
| 2012/0226074 A1 | | 9/2012 | Ho et al. |

FOREIGN PATENT DOCUMENTS

| | | | | |
|---|---|---|---|---|
| DE | 10336489 A1 | | 3/2005 | |
| EP | 1057509 A1 | | 12/2000 | |
| EP | 2311790 A1 | | 4/2011 | |
| EP | 1452518 B1 | | 6/2012 | |
| GB | 1130507 | | 10/1968 | |
| GB | 1130507 A | | 10/1968 | |
| GB | 1310544 A | * | 3/1973 | ............... B01D 3/18 |
| GB | 1310544 A | | 3/1973 | |

OTHER PUBLICATIONS

Emerson Process Management. "Improving Throughput." Improving Throughput with Digital Plant Architecture, www2.emersonprocess.com/siteadmincenter/PM%20Central%20Web%20Documents/plantweb-throughput.pdf.*
IPRP, Mailed Sep. 9, 2015 for PCT/US2014/044345.
ISR/WO, Issued Jun. 10, 2014 for PCT/US2014/044345.
Intellectual Property Office of Singapore; Search Report; Application No. 11201510267T; Date of completion of search: Nov. 8, 2016; 3 pages.
Intellectual Property Office of Singapore; Written Opinion; Application No. 11201510267T; Date of Written Opinion: May 9, 2016; 7 pages.
International Search Report for International Application No. PCT/US2014/044345; dated Oct. 6, 2014; Date of Completion: Sep. 29, 2014; 5 Pages.
Written Opinion of the International Searching Authority for International Application No. PCT/US2014/044345; International Filing Date: Jun. 26, 2014; Priority Date: Jun. 28, 2013; 6 Pages.

* cited by examiner

FOULING-RESISTANT DISTILLATION COLUMN AND PROCESS FOR THE MANUFACTURE OF COMPOUNDS

CROSS-REFERENCE TO RELATED APPLICATIONS

The present application claims the benefit of PCT/US2014/044345, filed on Jun. 26, 2014, which claims the benefit of U.S. Provisional Patent Application Ser. No. 61/840,840, filed on Jun. 28, 2013, the entire contents of which are hereby incorporated by reference.

BACKGROUND

This disclosure relates to a fouling-resistant distillation column and to a process for the manufacture of compounds, and in particular the manufacture of compounds such as (meth)acrylate esters using the distillation column.

Compounds such as acrylate and methacrylate esters (collectively, "(meth)acrylate esters") are used in a wide array of applications. Various systems are utilized in the manufacture of (meth)acrylate esters. These systems may involve a reaction step and a distillation step where the reaction step and distillation step may be integrated, to produce the (meth)acrylate ester from selected raw materials.

Distillation trays are used in the distillation column or in a distillation portion of the system to separate the product (e.g., the (meth)acrylate ester) from other materials therein. Distillation trays such as sieve trays, for example, are perforated metal plates with small holes that allow the gas from a reactive region to flow through the distillation column. Reactive liquid accumulates on the sieve trays and flows across the sieve trays and into a segmental downcomer directed below onto an adjacent sieve tray. However, during the distillation, fouling of the distillation trays with the materials accumulated thereon occurs over prolonged use. Reactive liquids, such as acid catalysts (e.g. sulfuric acid ($H_2SO_4$)) or by-products, may become entrained with the gas from the reactive region and may also accumulate on the distillation trays.

The accumulated materials clog the holes in the sieve trays, disrupting and/or impeding the flow of gas and liquid, resulting in an increase in the differential pressure, e.g., pressure drop, in the distillation column. The increase in differential pressure in turn leads to a decrease in production capacity over time until such point that the system is shut down for cleaning. In some systems, the period of time of such maintenance intervals for such cleaning is every few months.

Therefore, a need exists for a system and process which exhibits improved fouling resistance in the purification or manufacture of compounds such as (meth)acrylate esters, decreased differential pressure due to fouling of the system, increased production capacity and/or extended periods of time between maintenance clean outs.

SUMMARY

Disclosed herein is a fouling-resistant system for the manufacture of a compound from a reactant, the system comprising a reactant heating zone; and a distillation column in fluid communication with the reactant heating zone, the distillation column comprising a plurality of distillation trays for removing a by-product from the reactant and the compound; wherein at least 20% of the plurality of distillation trays are baffle trays arranged in a staggered configuration, where each tray contacts an opposing portion of an inner wall of the distillation column from a portion contacted by a tray located above the tray and below the tray; and the baffle trays are disposed in a lower portion of the distillation column.

Disclosed herein too is a fouling-resistant process for the manufacture of a compound from a reactant, the process comprising reacting the starting material in a reactant heating zone to generate a vapor phase; distilling the vapor phase in a distillation column, the distillation column being in fluid communication with the reactant heating zone; wherein the distillation column is comprised of a plurality of distillation trays for removing by-products from the starting material and the compound, where at least 20% of the plurality of distillation trays are baffle trays arranged in a staggered configuration, where each tray contacts an opposing portion of an inner wall of the distillation column from a portion contacted by a tray located above the tray and below the tray and the baffle trays are disposed in a lower portion of the distillation column; separating and removing a crude compound, water of reaction, unreacted starting materials, and by-products from the distillation column; and recovering the compound from the distillation column.

DETAILED DESCRIPTION

Disclosed herein is a fouling-resistant distillation column (hereinafter "distillation column"), where a portion of the distillation column comprises baffle trays instead of sieve trays. The distillation column may be used as part of a reaction system for the production of compounds such as (meth)acrylate esters. In an embodiment, the distillation column may include a reactant heating zone, or a combined reactant heating and reaction zone. In another embodiment, the distillation column is in fluid communication with a reaction vessel that functions as the reactant heating zone and a reaction zone. The distillation column may be mounted on the reaction vessel, or is external to the reaction vessel in fluid communication with the reaction vessel. The distillation column, along with the reaction vessel and other accessories (e.g., pumps, reboilers, condensers, and the like) will be referred to as a fouling-resistant system.

In an embodiment, one or more (or all) sieve trays in the distillation column are replaced with baffle trays. The use of baffle trays facilitates the cascading of liquids from one baffle tray to the next baffle tray in a waterfall type of flow. The baffle trays aid in the separation of unreacted starting materials, by-products, and the like, from the reaction product compound, which is then recovered for further processing, purification and/or use. The distillation column can be advantageously used to produce compounds such as (meth) acrylate esters with reduced differential pressure in the distillation column and minimal downtime, which leads to increased production efficiency and consequently to lower manufacturing costs.

Accordingly, a fouling-resistant process for the manufacture of a compound such as a (meth)acrylate ester using the distillation column is also disclosed. The process comprises heating a starting material in a liquid phase to generate a vapor phase. The vapor phase is distilled in the distillation column. The distillation column is used to separate and remove a crude reaction product, water of reaction, unreacted starting materials, and by-products from the distillation column using a plurality of baffle trays disposed within the distillation column. The baffle trays are anti-fouling trays because they prevent fouling of the sieve trays in the distillation column and minimize pressure differential within the distillation column. The plurality of trays in the distillation column comprise at least 20% baffle trays based on the total number of the trays. A product such as a (meth)acrylate ester is removed from the distillation column.

Figure 1:
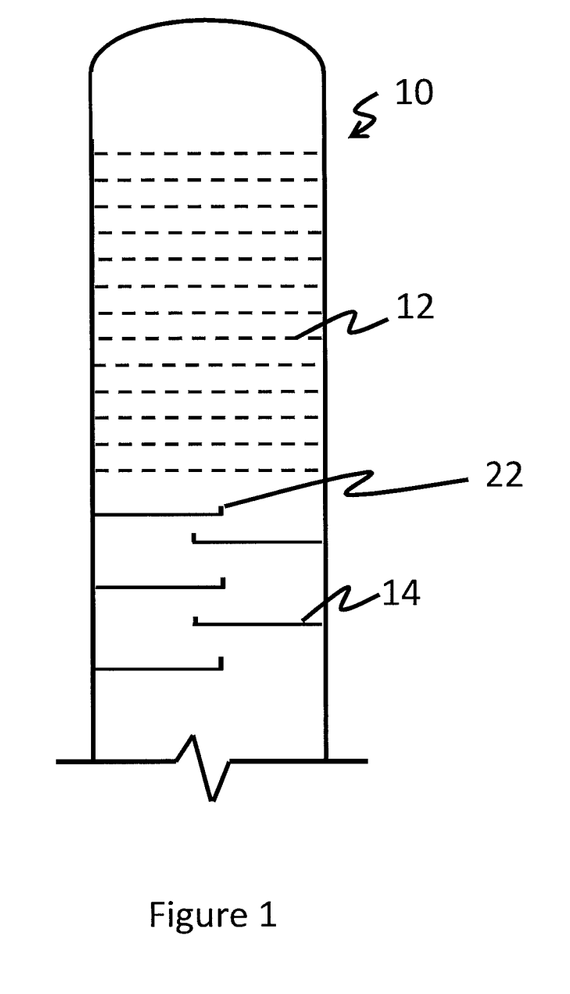
FIG. 1 is a side view of a longitudinal cross-section of the distillation column.

With reference to the FIG. 1, a distillation column 10 comprises a plurality of sieve trays 12 and a plurality of baffle trays 14, wherein one or more of the baffle trays 14 have a weir 22 at an edge thereof. The baffle trays 14 are disposed lower in the distillation column than the sieve trays 12. In an embodiment, the 20 percent of the sieve trays, specifically 15 percent of the sieve trays, and more specifically 10 percent of the sieve trays of a distillation column are replaced with baffle trays.

The baffle trays 14 are the lowermost trays in the distillation column 10. The sieve trays 12 lie above the baffle trays 14 in the distillation column 10. The number of baffle tray(s) is selected according to the particular application, equipment, and operating conditions. The baffle trays are located in the lower portion of the distillation column. In an embodiment, the lower two-thirds, specifically the lower half, and more specifically the lower one-fourth of the length of the distillation column 10 contains baffle trays. By disposing the plurality of baffle trays 14, in the lowermost position of the distillation column 10, a significant reduction in fouling of the system is obtained. Any baffle tray suitable for use in a distillation column may be employed. The shape and/or type of baffle tray is selected according to the particular application, equipment and operating conditions. Examples of suitable baffle trays, also known as "shower deck" trays, are a rod-type baffle tray, a plate-type baffle tray, a comb-type baffle tray, and the like, or a combination comprising at least one of the foregoing.

The baffle trays are disposed in a substantially horizontal position relative to the center or vertical axis of the distillation column. The baffle trays 14 are staggered, i.e., each succeeding tray contacts a different portion, specifically an opposing portion, of the inner wall of the distillation column from the portion contacted by a preceding tray and a succeeding tray in the line of fluid flow. In other words, each tray is located on a different, offset portion of the inner wall of the distillation column relative to the part of the wall contacted by the tray located immediately above it as well as the tray located immediately below it. This arrangement promotes a cascading effect, where liquid accumulated on one baffle tray 14 overflows onto the next baffle tray immediately below it, and where particulate matter is trapped by the tray. This process is repeated on all of the baffle trays located in the distillation column 10, thus trapping a significant amount of undesirable by-product without hindering the mobility of desired liquids within the distillation column 10. The precise position of the baffle trays relative to one another is selected according to the particular application, and may be uniform or non-uniform with regard to the distance there between in the vertical direction of the distillation column 10. In FIG. 1, each of the baffle trays 14 shown is a plate-type baffle tray in close contact at the arcuate edge thereof to an inner wall of the distillation column 10. Each of the baffle trays 14 is disposed substantially horizontally relative to, and is arranged at an equal interval, in the vertical direction of the distillation column 10.

In an embodiment, the distillation column 10 depicted in the FIG. 1 may be manufactured by retrofitting a portion of the sieve trays in an existing distillation column with baffle trays. The retrofit is accomplished by replacing the sieve trays in the lower portion of the distillation column 10. Alternatively, the distillation column 10 may be manufactured by methods known in the art.

Figure 2:
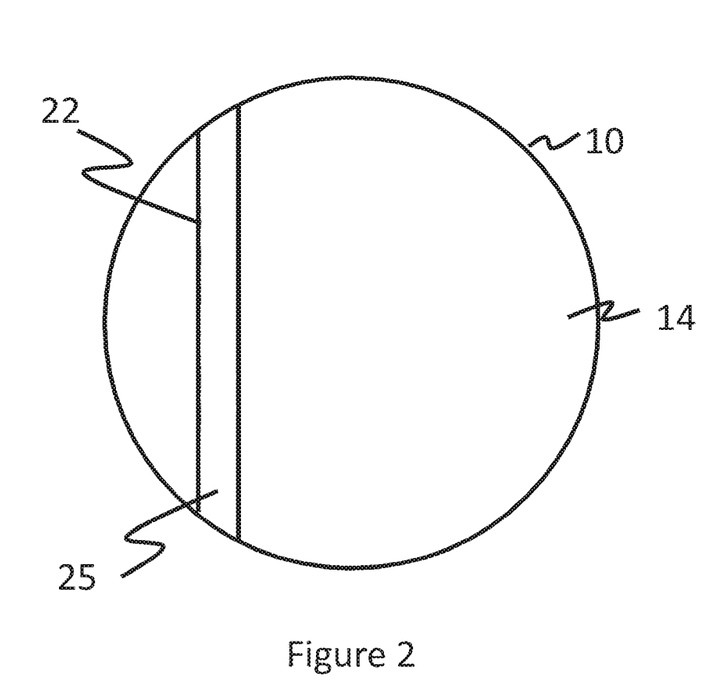
FIG. 2 is a top cross-sectional view of the distillation column and a baffle tray disposed therein.
Figure 3A:
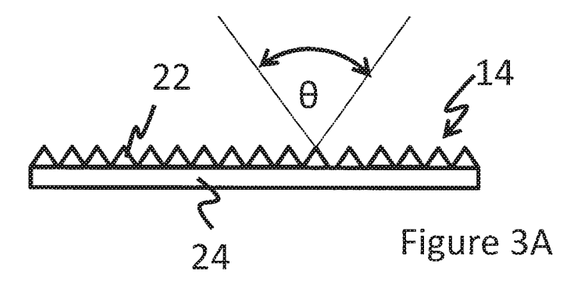
FIGS. 3A-3D are side views, in the direction of liquid flow across the surface of the baffle tray, of a single baffle tray having (A) a serrated weir configuration, (B) a smooth weir configuration, (C) a rectangular weir configuration, and (D) a rounded weir configuration.

The FIG. 2 depicts a top view of the distillation column. As can be seen in the FIG. 2, a baffle tray 14 covers 55% to 90%, specifically 58 to 85%, and more specifically 60 to 80% of the cross-sectional area of the distillation column 10. A baffle tray may generally have a "shower tray" configuration with an overflow weir 22 located at the edge of the baffle tray 14, for example a serrated weir. A support panel can be located in area 25. Thus, in an embodiment the body of the tray may be smooth with a serrated weir. Sludge material (e.g., polymeric material of various molecular weights and other solid particles) accumulate on a tray until the quantity is large enough where some amount will be washed off the tray with the cascading liquid, i.e., sludge and solid particulates will accumulate to a point where the cascading liquid moves them over the weir and flushes them down to the bottom of the distillation column, where they may be recycled or removed with the bottoms liquid stream. In an embodiment, as shown in FIG. 3A, the overflow weir is serrated. Further as shown in FIG. 3A, each serration has an angle $\theta$ of 75 to 100, specifically 85 to 95 degrees to an adjacent serration in an embodiment. The serrated configuration serves to inhibit the motion of the particles in the fluid. In other words, particles contained in the liquid will settle behind the weir and are separated from the liquid, which can then cascade to the bottom of the distillation column. Other particle-retaining configurations for the overflow weir can be used, for example flat-top (FIG. 3B), rectangular (FIG. 3C), rounded (FIG. 4D), irregular, and the like, or a combination of at least two configurations. In an embodiment, each of the baffle trays has a weir.

Figure 3B:
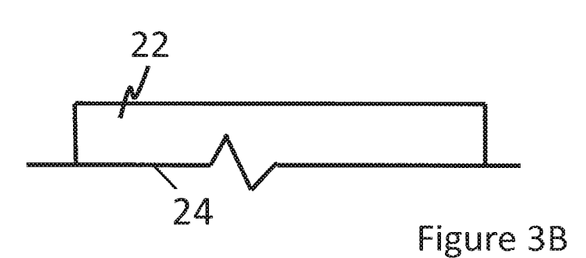
Figure 3C:
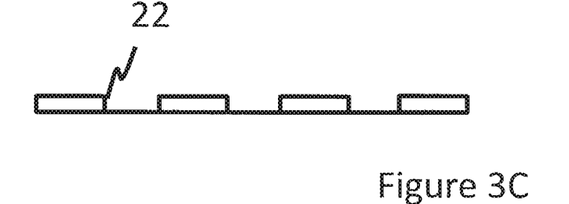
Figure 3D:
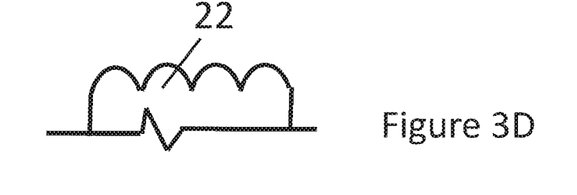

In another aspect as shown in FIG. 3A, the overflow weir 22 is disposed on a supporting panel 24, e.g., a vertical rib or I-beam-type structure. The supporting panel 24 can be a single panel or can comprise a plurality of panels (not shown). In this embodiment the overflow weir 22 can be fixedly attached to the supporting panel 24 by rivets, welding, adhesive, or the like, or can be removably attached by means of bolts, screws and nuts, or the like. Alternatively, the supporting panel 24 can also be formed from the edge of each baffle tray 14 by bending of the sheet material of the baffle tray 14. In still another embodiment, the entirety of the weir may be formed directly into the top edge of supporting panel 24 shown in FIG. 3B, for example by bending the edge of the panel (which, if desired. has been modified to have the desired particle-retaining configuration). In still another embodiment, the baffle itself can be bent or formed to provide an integrated weir and baffle, as represented in FIG. 3B.

Also as shown in the FIG. 3A, the entire edge of the baffle tray 14 comprises the serrations or other particle-retaining shapes. Alternatively, only a portion of the edge of the baffle tray may have the serrations or other particle-retaining shapes. Alternatively, only some or none of the baffle trays may have the serrations or other particle-retaining shapes. Non-limiting examples of such particle-retaining shapes include projections of any shape extending outward from the surface, indentations extending toward the surface, of any shape or size may be selected. Referring back to FIG. 3A, in an embodiment, the projections on the baffle trays in the plurality of baffle trays are hook-shaped, with the hooked portions opposed to the direction of flow in each baffle tray.

The distillation column 10 is in fluid communication with a reactant heating zone. The heating zone may be a heating zone or a combined reactant heating and reaction zone that forms an integral part of the distillation column (as shown, for example, in FIG. 4), or the heating zone may be separate from the reaction vessel (as shown, for example, in FIG. 5). As can be seen in the FIG. 4, the lower portion 16 of the distillation column is a heating zone or a combined heating/reaction zone, where reactants can be added and heated, or added, reacted, and heated, and from which products can be removed. Thus, in an embodiment, primarily heating or only heating occurs in zone 16, and reaction occurs in the tray portion, the distillation portion, or the tray and distillation portions of the column. In another embodiment, heating and reaction occurs in zone 16, although it may also occur in the tray portion, the distillation portion, or the tray and distillation portions of the column. The zone 16 can be heated externally to heat the starting material and/or to promote the reaction.

Figure 4:
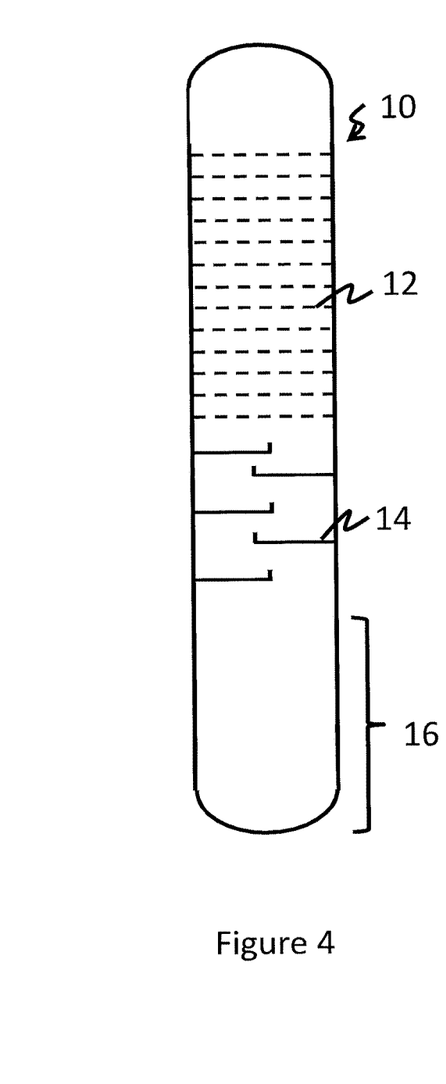
FIG. 4 is a side view of a longitudinal cross-section of an integrated reactant heating zone or heating/reaction zone and the distillation column.

Use of an integral heating or heating/reaction zone and distillation column as shown in FIG. 4 avoids a separate distillation step, which saves energy (e.g. for heating) and material costs. These integrated configurations are particularly useful for conducting equilibrium-limited reactions such as esterification and transesterification reactions. Production, or conversion, can be significantly increased due to the continuous removal of reaction products from a reactive zone in the reaction vessel 16. This configuration also improves the production capacity of the distillation column 10. The raw materials are selected according to their respective properties such as relative volatility, and the distillation temperature is selected according to the desired reaction product and production capacity.

Figure 5:
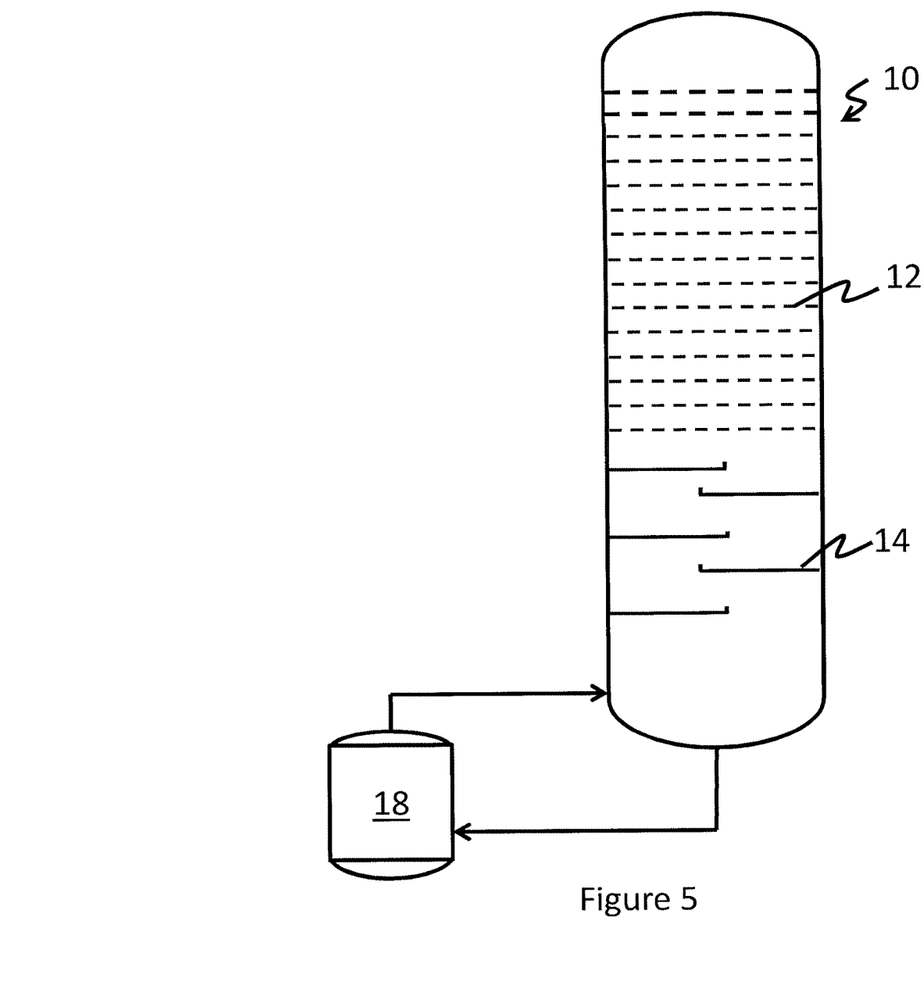
FIG. 5 is a side view of a longitudinal cross-section of the distillation column in fluid communication with an external reaction vessel.

In another embodiment, the heating zone is external to the distillation column. For example, the reactants can be heated separately and injected into the column and mixed in the column. In this embodiment, reaction occurs in the tray portion, the distillation portion, or the tray and distillation portions of the column. More commonly, the heating and reaction occurs in a separate reaction vessel. In these embodiments, the reaction vessel acts as the heating/reaction zone. For example the distillation column 10 may be mounted on the reaction vessel (not shown). Alternatively, the reaction vessel is in a recycle loop with the distillation column 10 as shown in FIG. 5. The FIG. 5 depicts a distillation column 10 that is separate from but in fluid communication with a reaction vessel 18. Reactants are charged to the reaction vessel, reacted, and vapors are transported to the distillation column 10, where products can be separated from vapors, reactants, and by-products. Products and by-products can be removed from the reaction vessel 18, and some by-products may be removed from the distillation column. Liquid collected at the bottom of the distillation column 10 can be routed back to the reaction vessel 18 for further processing. Additional components can be added to the distillation column to facilitate processing of the reactants. Non-limiting examples of such additional components include a reboiler, a condenser, a pump, a second reaction vessel, a second distillation column, a phase separator vessel, a conduit, a controller, a thermometer, a pressure gauge, or a combination thereof.

The distillation column 10 can be used for the manufacture of compounds such as (meth)acrylate esters and (meth)acrylic acids. As used herein, the use of the term "(meth)" followed by another term such as acrylate refers to both acrylates and methacrylates. For example, the term "(meth) acrylate" refers to either acrylate or methacrylate; the term "(meth)acrylic" refers to either acrylic or methacrylic; and the term "(meth)acrylic acid" refers to either acrylic acid or methacrylic acid. Examples of suitable (meth)acrylate esters include, but are not limited to, methyl methacrylate, ethyl methacrylate, hydroxyethyl methacrylate, butyl methacrylate, ethyl acrylate, 2-ethylhexyl acrylate, butyl acrylate, and the like. While (meth)acrylate esters are the focus of this disclosure, the distillation column is not limited thereto, and may be similarly applied to any applicable reaction and/or distillation process in which fouling resistance is desired, for example (meth)acrylic acids.

In the process for the manufacture of compounds such a (meth)acrylate ester, the starting materials (reactants), catalysts, solvents, accelerators, inhibitors, and other reactants that facilitate the manufacturing of the desired product are charged to the heating zone, the heating/reaction zone, or the reaction vessel and heated. In an embodiment, in one method of using the distillation column 10, starting materials and any other reactants are charged to the zone 16 of the distillation column (see FIG. 4), and in particular a heating reaction zone 16, or the reaction vessel 18 (see FIG. 5). The reactants are heated to a suitable temperature to generate vapors that are released into the distillation column. Reaction can occur in the heating zone or the reaction vessel, in the distillation column, or both. The product compound is then distilled to remove starting materials, by-products, and the like. Distillation is a method of separating mixtures based on differences in volatility of the components in the boiling liquid mixture, and in this regard is a vapor/liquid equilibrium-driven separation process, rather than a chemical reaction.

Whether distillation in the distillation column is conducted as a separate step (as depicted in the FIG. 5) or is integrated with the heating zone (as seen in the FIG. 4), the vapors in the vapor phase generated in the reaction vessel or heating zone are routed to the distillation column. Following distillation, the desired product (e.g., the (meth)acrylate ester) is removed from an overhead portion of the distillation column. The (meth)acrylate ester may also be subjected to further purification and/or processing to remove lighter molecular weight reaction by-products ("lights") which may also be extracted with the (meth)acrylate ester reaction product from the distillation column.

Starting materials, reaction products, and/or by-products may become entrained with the vapor phase as it enters the distillation column. Undesired particles (by-products) can also be produced in the distillation column as reactants travel through the distillation column. As discussed further below, when a sieve tray is used as the lowermost distillation tray, polymers and other solid materials can foul the lower distillation trays by blocking the openings in the tray where vapors must pass, eventually rendering the distillation process inoperable. (Meth)acrylate esters are particularly susceptible to undesirable polymerization in acrylate manufacturing plant (or system) conditions when condensed acrylate vapors accumulate in liquid pools or films containing reduced concentrations of polymerization inhibitors.

The plurality of baffle trays separate and hold heavier molecular weight reaction by-products ("heavies," having a greater molecular weight than the desired product), unreacted materials and other by-products, as well as other materials which may be included in or entrained, such as sulfuric acid ($H_2SO_4$), in the vapor phase as the vapor phase proceeds through the distillation column. The baffle trays can be removed from the distillation column for cleaning when substantially covered with heavies.

The selection and implementation of the plurality of baffle trays in the lower region of the distillation column results in reduced fouling of systems used for the manufacture of (meth)acrylate esters. As a result of the reduced fouling of the plurality of distillation trays, increases and/or fluctuations in differential pressure in the distillation column are reduced.

In an embodiment, the differential pressure in the distillation column is less than 100 dP units (e.g., inches of water or millimeters (mm) of mercury (Hg)). In another embodiment, the differential pressure in the distillation column is less than 80 dP units. In yet another embodiment, the differential pressure in the distillation column is less than 50 dP units. In still yet another embodiment, the differential pressure in the distillation column is less than 25 dP units. In an embodiment, the differential pressure in the distillation column is 6 to 100 dP units, specifically 8 to 80 dP units, and more specifically 10 to 60 dP units. In a specific embodiment, the dP units are mm Hg.

The anti-fouling properties imparted by the baffle trays described herein further results in extending the period of time between maintenance clean-outs. The fouling resistance properties imparted by baffle trays described herein further also results in an improvement in the column throughput rate and consequently, in production capacity. In an embodiment, the reduction in the distillation column production rate is less than 40% of the maximum production rate between maintenance clean-outs. In another embodiment, the reduction in the distillation column is less than 30% of the maximum production rate between maintenance clean-outs. In yet another embodiment, the reduction in the distillation production rate column is less than 20% of the maximum production rate between maintenance clean-outs, when compared with a distillation column that does not contain baffle trays.

The use of baffle trays in the distillation column for the manufacture of (meth)acrylate esters therefore provides several advantages over other systems used for the manufacture of (meth)acrylate esters, including but not limited to, improved column throughput, improved vapor flow, reduced fouling, reduced entrainment, reduced overall differential pressure, and/or fluctuations thereof.

EXAMPLES

Example 1

This comparative example was conducted to demonstrate the differential pressure over time using a comparative system for the manufacture of butyl acrylate. An integrated heating/reaction zone and distillation column equipped with three sieve trays disposed in a lower portion of the distillation column. The differential pressure in the distillation column was measured over a period of time of 45 days. The differential pressure (dP) was measured on a scale ranging from 0 to 140 mm Hg using a commercially available instrument. The results of the differential pressure in the distillation column plotted against time are provided in the graph in FIG. 6.

Figure 6:
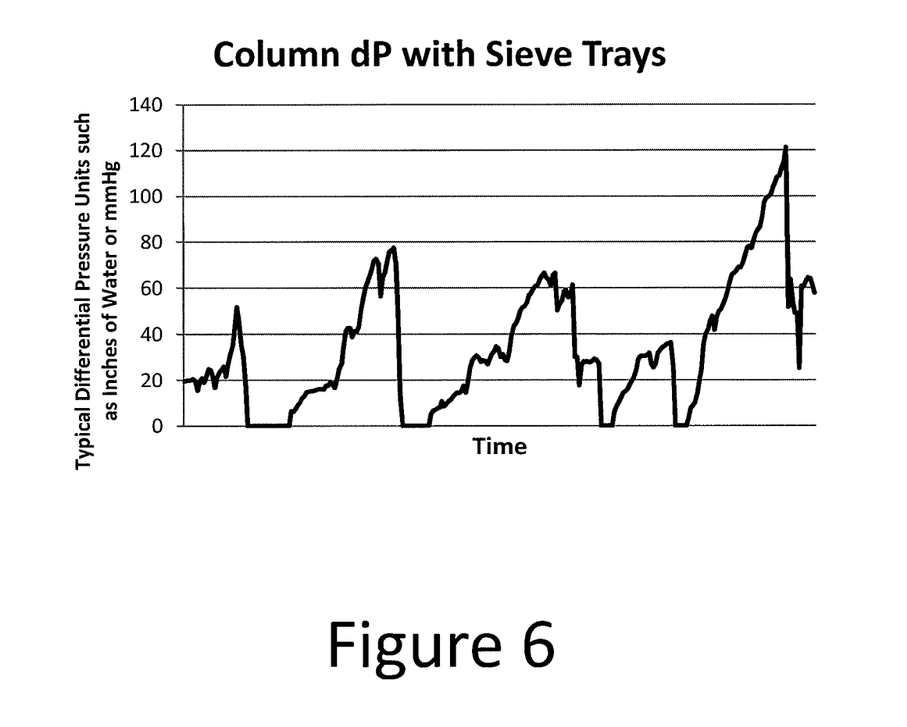
FIG. 6 is a graph depicting the differential pressure (on a scale ranging from 0 to 140 mm Hg) over time of a comparative system used in the manufacture of (meth)acrylate esters.

As can be seen from FIG. 6, the differential pressure in the distillation column fluctuates significantly over time. As shown in FIG. 6, the initial dP, or clean column dP, was 6 dP units. The results provided in FIG. 6 also show that the overall differential pressure increase significantly over time, ranging from about 20 to about 50 dP units during the initial use of the distillation column to up to about 120 dP units toward the end of the period of time during which the distillation column was used. After the dP in the distillation column exceeded 70 dP units over a period of 45 days, the system was shut down for cleaning. The total period of time in the graph depicted in FIG. 6 is 290 days. A total of four shut-down periods occurred during this overall period of time, as reflected during the periods in which the differential pressure was 0 dP units in FIG. 6. During periods of high product demand during this period of operation, the column throughput rate was reduced by up to 50% of the clean column throughput rate in order to extend the operating time.

The significant fluctuations and high differential pressure which occurs over time due to fouling of the comparative system results in reduced production capacity, leading to more frequent maintenance intervals (shutdowns) in order to remove the accumulated deposits.

Example 2

This example was conducted to demonstrate the differential pressure over time using an embodiment of the fouling-resistant system described herein for the manufacture of butyl acrylate. The integrated heating/reaction zone and distillation column described above in Example 1 was used, with the exception that all of the sieve trays utilized in Example 1 were replaced with baffle trays. The distillation column was thus equipped with three baffle trays. The differential pressure in the distillation column was measured over a period of time of 290 days. The differential pressure (dP) was measured on the same scale and using the same differential pressure instrument as described above with regard to Example 1. The results of the differential pressure in the distillation column plotted against time are provided in the graph in FIG. 7.

Figure 7:
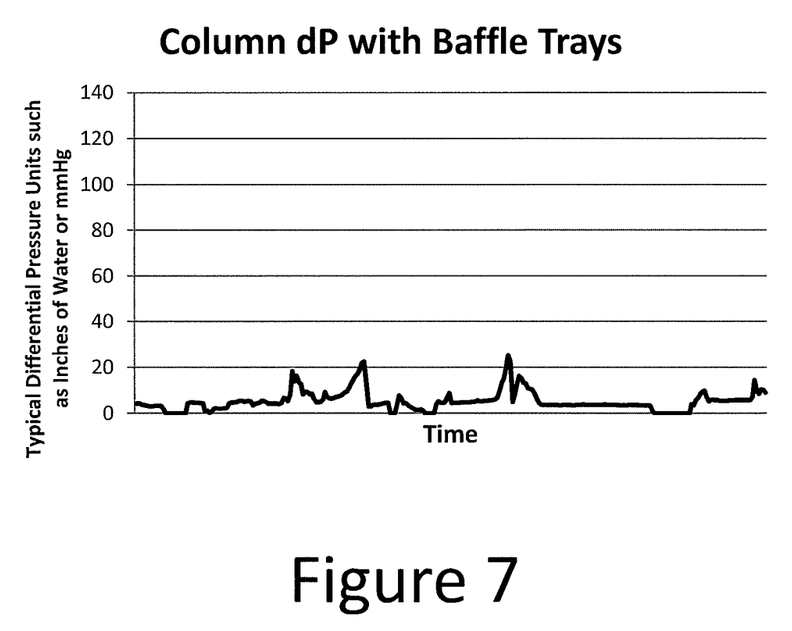
FIG. 7 is a graph depicting the differential pressure (on a scale ranging from 0 to 140 mm Hg) over time of the fouling-resistant system for the manufacture of (meth)acrylate esters according to an embodiment of the invention.

As can be seen from FIG. 7, the differential pressure in the distillation column does not fluctuate significantly over time in comparison to the comparative system of Example 1. The results provided in FIG. 7 also show that the overall differential pressure is relatively constant over time, ranging from about 0 to about 25 dP units during the total time during which the distillation column was used.

Figure 8:
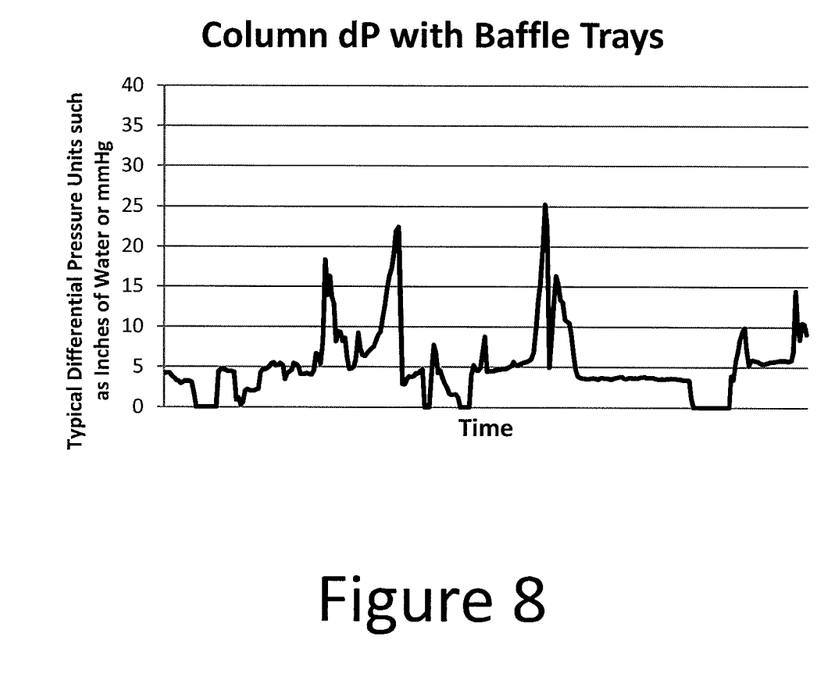
FIG. 8 is a graph depicting the differential pressure (on a scale ranging from 0 to 40 mm Hg) over time of the fouling-resistant system for the manufacture of (meth)acrylate esters according to an embodiment of the invention.

These results are further exemplified in the graph provided in FIG. 8, in which the same results are plotted on a smaller dP scale ranging from 0 to 40 mm Hg. The results in FIG. 8 further show that fluctuations in the dP which occur over time are generally much smaller than those shown for the comparative system of Example 1. As can be seen by a comparison of FIG. 6 with FIG. 7, the fluctuations shown in FIG. 7 (as well as FIG. 8) are believed to be due to relatively normal fluctuations in the vapor or liquid flow rates (or column operating rate) which occur during the distillation process. When the vapor flow rate was reduced, the dP in the distillation column would return to a clean column dP baseline level.

The relatively constant and reduced overall differential pressure of the fouling-resistant system demonstrates that reduced fouling has occurred in the system relative to the comparative system of Example 1. The system for the reduction of fouling in the manufacture of (meth)acrylate esters thus significantly improves production capacity of the (meth)acrylate ester produced therefrom and significantly extended the period of time for maintenance intervals between system clean-outs to over 200 days.

Various specific exemplary embodiments are set forth below.

Embodiment 1

A fouling-resistant system for the manufacture of a compound comprising: reactant heating zone; and a distillation column in fluid communication with the reactant heating zone; wherein the distillation column comprises a plurality of distillation trays for removing by-products from the compound, at least 20% of the plurality of distillation trays are baffle trays arranged in a staggered configuration, each tray contacts a different portion of an inner wall of the distillation column from a portion contacted by a tray located above the tray and below the tray, and the baffle trays are disposed in a lower portion of the distillation column.

Embodiment 2

The fouling-resistant system of embodiment 1, where an edge or a portion of an edge of the baffle tray comprises a particle-retaining configuration.

Embodiment 3

The fouling-resistant system of any of embodiments 1-2, wherein a baffle tray occupies 55 to 90 percent of the cross-sectional area of the distillation column at its location in the distillation column.

Embodiment 4

The fouling-resistant system of any of embodiments 1-3, wherein the heating zone is a combined heating/reaction zone integrated with the distillation column.

Embodiment 5

The fouling-resistant system of any of embodiments 1-4, wherein the heating zone is a reactor in fluid communication with the distillation column.

Embodiment 6

The fouling-resistant system of any of embodiments 1-5, wherein the differential pressure in the distillation column is less than 100 dP units.

Embodiment 7

The fouling-resistant system of any of embodiments 1-6, wherein the differential pressure in the distillation column is 6 dP units to 100 dP units.

Embodiment 8

The fouling-resistant system of any of embodiments 1-7, wherein a production capacity column throughput rate reduction in the distillation column is less than 20% of the maximum production rate between maintenance intervals.

Embodiment 9

A fouling-resistant process for the manufacture of a compound, the process comprising: heating a reactant in a heating zone to generate a vapor phase; distilling the vapor phase in a distillation column, the distillation column being in fluid communication with the heating zone; wherein the distillation column comprises a plurality of distillation trays for removing by-products from the reactant and the compound, at least 20% of the plurality of distillation trays are baffle trays arranged in a staggered configuration, each tray contacts an opposing portion of an inner wall of the distillation column from a portion contacted by a tray located above the tray and below the tray, and the baffle trays are disposed in a lower portion of the distillation column; separating and removing a crude compound, water of reaction, unreacted raw materials, and a by-product from the distillation column; and recovering the compound from the distillation column.

Embodiment 10

The fouling-resistant system of embodiment 9, wherein the differential pressure in the distillation column is less than 100 dP units.

The invention claimed is:
1. A system for the manufacture of a compound comprising:
   a reactant heating zone; and
   a distillation column in fluid communication with the reactant heating zone;
   wherein
   the distillation column comprises a plurality of distillation trays for removing by-products from the compound, the plurality of distillation trays comprising a plurality of sieve trays and a plurality of baffle trays;
   at least 20% of the plurality of distillation trays are baffle trays arranged in a staggered configuration,
   each baffle tray contacts a different portion of an inner wall of the distillation column from the baffle trays located immediately above and/or below each baffle tray, and
   all of the baffle trays are disposed in the lower half of the distillation column,
   wherein any baffle tray occupies 55 to 90% of the cross-sectional area of the distillation column at the location of the baffle tray in the distillation column.

2. The system of claim 1, where an edge or a portion of an edge of a baffle tray comprises a particle-retaining configuration.

3. The system of claim 1, wherein the reactant heating zone is a combined heating/reaction zone integrated with the distillation column.

4. The system of claim 1, wherein the reactant heating zone is a reactor in fluid communication with the distillation column.

5. The system of claim 1, wherein a differential pressure in the distillation column is less than 100 dP units.

6. The system of claim 1, wherein a differential pressure in the distillation column is 6 dP units to 100 dP units.

7. The system of claim 1, wherein the baffle trays are shower deck trays.

8. The system of claim 1, wherein the baffle trays are shower deck trays selected form the group consisting of rod-type baffle trays, plate-type baffle trays, comb-type baffle trays, and a combination thereof.

9. A process for the manufacture of a compound, the process comprising:

heating a reactant in a heating zone to generate a vapor phase;

distilling the vapor phase in a distillation column, the distillation column being in fluid communication with the heating zone; wherein the distillation column comprises a plurality of distillation trays for removing by-products from the reactant and the compound, the plurality of distillation trays comprising a plurality of sieve trays and a plurality of baffle trays;

at least 20% of the plurality of distillation trays are baffle trays arranged in a staggered configuration, each baffle tray contacts a different portion of an inner wall of the distillation column from the baffle trays located immediately above and/or below each baffle tray, and all of the baffle trays are disposed in the lower half of the distillation column;

separating and removing a crude compound, water of reaction, unreacted raw materials, and a by-product from the distillation column; and recovering the compound from the distillation column, wherein any baffle tray occupies 55 to 90% of the cross-sectional area of the distillation column at the location of the baffle tray in the distillation column.

10. The process of claim 9, wherein the differential pressure in the distillation column is less than 100 dP units.

* * * * *